(12) United States Patent
Isola et al.

(10) Patent No.: US 10,744,344 B2
(45) Date of Patent: Aug. 18, 2020

(54) ADAPTIVE RADIATION THERAPY PLANNING

(71) Applicant: KONINKLIJKE PHILIPS N.V., Eindhoven (NL)

(72) Inventors: Alfonso Agatino Isola, Eindhoven (NL); Pedro Jorge Da Silva Rodrigues, Veldhoven (NL); Davide Fontanarosa, Neerpelt (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 29 days.

(21) Appl. No.: 16/086,680

(22) PCT Filed: Mar. 29, 2017

(86) PCT No.: PCT/EP2017/057381
§ 371 (c)(1),
(2) Date: Sep. 20, 2018

(87) PCT Pub. No.: WO2017/167794
PCT Pub. Date: Oct. 5, 2017

(65) Prior Publication Data
US 2019/0099620 A1    Apr. 4, 2019

(30) Foreign Application Priority Data
Mar. 30, 2016  (EP) ..................... 16162765

(51) Int. Cl.
*A61N 5/10*  (2006.01)
(52) U.S. Cl.
CPC ......... *A61N 5/1038* (2013.01); *A61N 5/1037* (2013.01); *A61N 5/1067* (2013.01); *A61N 5/1071* (2013.01); *A61N 5/1075* (2013.01)

(58) Field of Classification Search
CPC .. A61N 5/1038; A61N 5/1067; A61N 5/1037; A61N 5/1071; A61N 5/1075
See application file for complete search history.

(56) References Cited

U.S. PATENT DOCUMENTS

| | | | |
|---|---|---|---|
| 7,221,733 | B1 | 5/2007 | Takai et al. |
| 8,135,111 | B2 | 3/2012 | Jaffray et al. |

(Continued)

FOREIGN PATENT DOCUMENTS

EP    1977788 A2    10/2008

OTHER PUBLICATIONS

Bortfield, T. et al., "Decomposition of pencil beam kernals for fast dose calculations in three-dimensional treatment planning". Medical Physics, vol. 20, No. 2, Pt. 1, Mar./Apr. 1993.

(Continued)

*Primary Examiner* — Kiho Kim

(57) ABSTRACT

The invention relates to system and a method for adapting a radiotherapy treatment plan for treating a target structure within a target region of a patient body, where a planning unit (7) adapts the treatment plan on the basis of a set of influence parameters quantifying an influence of the radiation on the target region per unity intensity emission in accordance with an anatomical configuration of the target region. In a storage (8), a plurality of sets of influence parameters is stored, each set being associated with an image of the body region representing a particular anatomical configuration of the target region and the planning unit (7) is configured to select the set of influence parameters from the stored sets on the basis of a comparison between a captured image of the body region and at least one of the images associated with the sets of influence parameters.

20 Claims, 1 Drawing Sheet

(56) References Cited

U.S. PATENT DOCUMENTS

| | | | |
|---|---|---|---|
| 8,744,045 B2 | 6/2014 | Nord et al. | |
| 9,192,786 B2* | 11/2015 | Yan | A61N 5/1037 |
| 9,814,908 B2 | 11/2017 | Siljamaki et al. | |
| 2007/0201613 A1 | 8/2007 | Lu | |
| 2013/0216026 A1 | 8/2013 | Nord et al. | |
| 2015/0283403 A1* | 10/2015 | Kapatoes | A61N 5/1071 600/1 |
| 2015/0367145 A1* | 12/2015 | Sjolund | A61N 5/1038 600/1 |
| 2016/0217595 A1* | 7/2016 | Han | G06T 11/003 |
| 2016/0256714 A1* | 9/2016 | Field | A61N 5/1075 |
| 2017/0050051 A1 | 2/2017 | Berbeci et al. | |
| 2017/0169985 A1 | 6/2017 | Bachmann et al. | |
| 2017/0232274 A1 | 8/2017 | Isola et al. | |

OTHER PUBLICATIONS

Mcnutt, T.R. et al, "Modeling Dose Distributions from Portal Dose Images using the Convolution/Superposition Method", Medical Physics, vol. 23, Issue 8, Aug. 1996, Abstract.

Nawrocki, S. et al., "Clinical study and numerical simulation of brain cancer dynamics under radiotherapy", Commun Nonlinear Sci Numer Simulat 22 (2015) 564-573.

Liu, Y. et al., "Patient Specific Tumor Growth Prediction Using Multimodal Images", Medical Image Analysis 18 (2014) 555-565.

Yock, A.D. et al., "Forecasting longitudinal changes in oropharyngeal tumor morphology throughout the course of head and neck radiation therapy", Medical Physics, 2014 41(8): 061708-1-061708-11.

Ng, J.A. et al., "Kilovoltage intrafraction monitoring for prostate intensity modulated arc therapy: first clinical results", Int. J. Radiat. Oncol. Biol. Phys. Dec. 1, 2012; 84(5) e655-e661.

Noel, C. et al., "Prediction of intrafraction prostate motion: accuracy of pre- and post-treatment imaging and intermittent imaging", Int. J. Radiat. Oncol. Biol. Phys. vol. 73, Issue 3, Mar. 1, 2009, Abstract.

Langen, K.M. et al., "Correlation between dosimetric effect and intrafraction motion during prostate treatments delivered with helical tomotherapy", Phys. Med. Biol. (2008) 53 7073-86.

Huang, E.H. et al., "Late rectal toxicity: dose-volume effects of conformal radiotherapy for prostate cancer", Int. J. Radiat. Oncol. Biol. Phys. vol. 54, Issue 5 Dec. 1, 2002, Abstract.

Miles, E.F. et al., "Hypofractionation for prostate cancer: a critical review", Semin. Radiat. Oncol. (2008) 18 41-7.

Mutanga, T.F. et al., "Day-to-day reproducibility of prostate intrafraction motion assessed by multiple kV and MV imaging of implanted markers during treatment", Int. J. Radiat. Oncol. Biol. Phys. (2007) 68 1199-206.

Pflugfelder, D. et al., "A comparison of three optimization algorithms for intensity modulated radiation therapy", Z. Med. Phys. (2008) vol. 18, No. 2, pp. 111-119.

Yu, C.X. et al., "The effects of intra-fraction organ motion on the delivery of dynamic intensity modulation", Phys. Med. Biol. (1998) 43, Abstract.

Waghorn, B.J et al., "A computational method for estimating the dosimetric effect of intra-fraction motion on step-and-shoot IMRT and compensator plans", Phys. Med. Biol. (2010) 55 Abstract.

Nederveen, A.J. et al., "Measurements and clinical consequences of prostate motion during a radiotherapy fraction", Int. J. Radiat. Oncol. Biol. Phys. vol. 53, Issue 1, May 1, 2002, Abstract.

Reggiori, G. et al., "Cone beam CT pre- arid post-daily treatment for assessing geometrical arid dosimetric intrafraction variability during radiotherapy of prostate cancer", Journal of Applied Clinical Medical Physics vol. 12, No. 1, Winter 2011, p. 141-152.

Huang, K. et al., "Inter- and intrafraction uncertainty in prostate bed image-guided radiotherapy", International Journal of Radiation Oncology Biology Physics, vol. 84, Issue 2, Oct. 1, 2012, Abstract.

Bittner, N. et al., "Electromagnetic tracking of intrafraction prostate displacement in patients externally immobilized in the prone position", International Journal of Radiation Oncology Biology Physics, vol. 77, Issue 2, Jun. 1, 2010, Abstract.

Kron, T. et al., "Intra-fraction prostate displacement in radiotherapy estimated from pre- and post-treatment imaging of patients with implanted fiducial markers", Radiotherapy and Oncology 95 (2010) 191-197.

Litzenberg, D.W. et al., "Prostate intrafraction translation margins for real-time monitoring and correction strategies", Prostate Cancer vol. 2012, Article ID 130579, 6 pages.

Low, D.A. et al., "A technique for the quantitative evaluation of dose distributions." Med Phys. May 1998;25(5):656-61.

* cited by examiner

ADAPTIVE RADIATION THERAPY PLANNING

CROSS-REFERENCE TO PRIOR APPLICATIONS

This application is the U.S. National Phase application under 35 U.S.C. § 371 of International Application Serial No. PCT/EP2017/057381, filed on Mar. 29, 2017, which claims the benefit of European Patent Application No. 16162765.8, filed on Mar. 30, 3016. This application is hereby incorporated by reference herein.

FIELD OF THE INVENTION

The invention generally relates to a planning of an external beam radiation therapy treatment of a patient. More specifically, the invention relates to a system, a method and a computer program for adapting a radiotherapy treatment plan for a patient.

BACKGROUND OF THE INVENTION

In external beam radiation therapy, ionizing radiation is applied to target structures, such as tumors, within patients' bodies in order to control growth of or kill cancer cells. The radiation treatment is usually delivered in plural sessions, which are also referred to as treatment fractions in the art. In more advanced types of radiation therapy, such as so called intensity-modulated radiation therapy (IMRT), precise doses of radiation are applied to regions of the patient's body. In this respect, it is typically the goal to deliver a sufficiently high radiation dose to the target structure and to spare sensitive structures, such as organs, in the vicinity of the target structure as far as possible.

The treatment parameters for delivering the radiation and controlling the radiation treatment device are defined in a treatment plan. The treatment plan is generated in a planning system, which may particularly use a so-called inverse planning procedure. In such a procedure, the target structure and the surrounding structures to be spared are identified and treatment goals are specified. Such treatment goals include objectives which may specify requirements for the radiation dose delivered to certain regions of the patient, and/or constraints for the radiation doses delivered to certain regions. Then, an optimization process is carried out to find the treatment plan which fulfills the specified treatment goals. This optimization process is usually an operator-guided procedure in which an operator (e.g. a physician) reviews the dose distribution resulting from the treatment plan in several steps and makes changes to the treatment goals in order to find the optimal dose distribution.

Conventionally, such an inverse planning procedure is carried out on the basis of a stationary anatomical configuration of the region of interest, which does not change during the radiation treatment. However, the anatomical configuration of the region of interest does usually change during the radiation treatment. So, the delineation of a tumor changes due to its natural progression, which normally results in a growth of the tumor, and, most notably, due to the effects of the radiation therapy, which result in a (net) shrinkage of the tumor. Moreover, the position of the tumor can change during the time period between the delivery of two treatment fractions (so called inter-fraction motion) and relevant motion of the tumor can also occur during a single treatment fraction (so-called intra-fraction motion). The magnitude of such intra-fraction motion varies with the duration of the treatment fractions and usually also dependents on the body region comprising the tumor. One body region where larger magnitudes of intra-fraction motion of a tumor can occur is the prostate.

If the original treatment plan generated on the basis of the (stationary) anatomical configuration is used after shrinkage of the target structure and/or tumor motion, there is a high risk to affect healthy tissue by applying a high radiation dose to such tissue.

One approach for addressing this problem is the so-called adaptive radiation therapy. In accordance with this approach images of the region of interest are captured during the course of the radiation therapy in order to determine the changed anatomical configuration. Then, a re-planning procedure is carried out to adapt the treatment plan to the changed anatomical configuration. However, the re-planning procedure usually involves a very high computational complexity. In particular, it comprises a determination of the so-called influence matrix for the captured image. For each volume element (voxel) of the region of interest, the influence matrix quantifies the amount of dose absorbed by this voxel per unit intensity emission from all parts of the radiation beam (so-called beamlets). Due to the computational complexity involved particularly in the calculation of this matrix, the re-planning procedure is usually very slow.

Therefore, the re-planning in adaption radiation therapy has to be made "offline", i.e. between the treatment fractions. As consequence, it is only possible to account for inter-fractional changes of the anatomical configuration of the region of interest, such as changes of the delineation of the target structure between two treatment fractions and inter-fraction motion of the target structure. However, it is not possible (without undue effort) to take account of intra-fractional changes of the anatomical configuration of the region of interest.

EP 1 977 788 A2 discloses a system for delivering radiation therapy to a moving region of interest. The system generates a set of 4D treatment plans for different breathing tracks of the region of interest, where each plan is optimized for a one breathing track. During the treatment delivery, the appropriate plan is particularly selected on the basis of a determined position of the region of interest, where the system particularly determines a track of the region of interest on the basis of the position data and selects the plan corresponding the determined track.

SUMMARY OF THE INVENTION

It is an object of the present invention to allow for a computationally less complex re-planning of a radiation therapy treatment in case the anatomical configuration of the irradiated region of the patient body changes during the treatment.

In one aspect, the invention suggests a system for adapting a radiotherapy treatment plan for treating a target structure within a target region of a patient body, the treatment plan comprising irradiation parameters for controlling a delivery of radiation to the target region. The system comprises: (i) a planning unit configured to adapt the treatment plan on the basis of a set of influence parameters quantifying an influence of the radiation on the target region per unit intensity emission in accordance with an anatomical configuration of the target region, (ii) a storage for storing a plurality of sets of influence parameters, each set being associated with an image of the body region representing a particular anatomical configuration of the target region, and (ii) an imaging unit configured to acquire an image of the body region. The planning unit is configured to select the set of influence parameters from the stored sets on the basis of a comparison between the captured image and at least one of the images associated with the sets of influence parameters.

Since the planning unit uses influence parameters that are stored in a storage of the system, it does not have to calculate the influence parameters when adapting the treatment plan. Thus, the radiotherapy treatment can be re-planned on the basis of the acquired image of the target region and the re-planning involves less computational complexity. Each set of influence parameters may comprise components of an influence matrix. These components may be pre-computed prior to the radiotherapy treatment and stored in the storage of the system in association with the images.

In one embodiment, the radiation therapy treatment is delivered in a plurality of time intervals and the planning unit is configured to determine updated irradiation parameters for controlling the delivery of the radiation to the target structure in a k-th time interval. Here, the k-th time interval may be any time interval of the radiotherapy treatment. Thus, the planning unit can determine the irradiation parameters for a certain time interval on the basis of an image, which may be acquired just prior to the time interval.

In a further embodiment, the planning unit is configured to determine only the irradiation parameters for the k-th time interval on the basis of the selected set of influence parameters. In this embodiment, the irradiation parameters for the k-th time interval are the only variable parameters to be determined when adapting the treatment plan. This allows for further reducing the computational complexity as compared to a procedure which includes updating larger portions of the treat plan (e.g. the k-th and the subsequent time intervals).

In one embodiment, a relative orientation between a radiation beam and the target structure changes during the radiotherapy treatment, and each time interval corresponds to a period with a constant relative orientation between the radiation beam and the target structure. Such a period is also referred to as a view. In this embodiment, the planning unit can effectively perform a "single-view optimization" of the treatment plan, i.e. it can specifically optimize the irradiation parameters for a certain (k-th) view.

In one embodiment, the planning unit is configured to determine the updated irradiation parameters on the basis of a radiation dose distribution delivered to the target region during the radiotherapy treatment prior to the k-th time interval. In particular, the previously delivered radiation dose distribution may have been delivered using irradiation parameters determined on the basis of previously acquired images and associated stored influence parameters. In this case, the planning unit may obtain the previously delivered radiation dose distribution in accordance with the emitted fluence corresponding to these irradiation parameters and the stored set of influence parameters used for determining these irradiation parameters.

Further, the future dose distribution to be delivered in subsequent time intervals should be taken into consideration in order to accurately determine optimized irradiation parameters for a certain time interval. In this regard, one embodiment comprises that the system is further configured to provide an estimate of a radiation dose distribution delivered to the target region in subsequent time intervals following the k-th time interval, and that the planning unit is configured to determine the irradiation parameters for the k-th time interval on the basis of said estimate.

In a related embodiment, the estimate is derived from an initial treatment plan determined prior to the radiotherapy treatment, particularly from an emitted fluence specified in the initial treatment plan for the subsequent time intervals. In further related embodiment, the estimate of the subsequently delivered radiation dose distribution is based on one predetermined anatomical configuration of the target region. This anatomical configuration may correspond to an anatomical configuration determined prior to the radiotherapy treatment, such as, for example, the anatomical configuration on the basis of which the aforementioned initial treatment plan has been generated. This approach significantly reduces the computational complexity for estimating the subsequently delivered radiation dose distribution.

In a further embodiment, the system is further configured to provide plural estimates of the radiation dose distribution delivered to the target region in subsequent time intervals, each estimate being associated with the k-th time interval and one set of influence parameters, wherein the planning unit is configured to determine the treatment plan on the basis of the estimate associated with the selected set of influence parameters.

For each set of influence parameters, the estimate may be determined using the selected set of influence parameters under the assumption that this set of influence parameters is valid for all subsequent time intervals, i.e. the assumption that the anatomical configuration of the target region does not change during the subsequent time intervals. This approach allows for a more accurate estimate of the future dose distribution compared, while it also requires a relatively low computation complexity.

As an alternative, the estimates may be based on predictions of the anatomical configuration of the target region in the subsequent time intervals, the predication being made using a model quantifying changes of the anatomical configuration of the body as a function of time. This approach allows for an even more accurate estimate of the future dose distribution, but also involves a higher computational complexity.

In any case, the estimate or plural estimates can be pre-computed prior to the radiotherapy treatment and may be pre-stored in the storage of the system. Thus, the estimates do not have to be computed during the radiotherapy treatment so that a fast update of the treatment plan is possible.

In one embodiment, the planning unit is configured to select the set of influence parameters associated with an image that has the largest similarity with the captured image in accordance with a predefined similarity measure. In principle, any suitable similarity measure known to the person skilled in the art may be used, particularly an image-based, an anatomy-based and/or geometry similarity measure.

In a further aspect, the invention suggests a method for adapting a radiotherapy treatment plan for treating a target structure within a target region of a patient body, the treatment plan comprising irradiation parameters for controlling a delivery of radiation to the target region. The method comprises:

storing a plurality of sets of influence parameters in a planning unit, the influence parameters quantifying an influence of the radiation on the target region per unit intensity emission in accordance with an anatomical configuration of the target region and each set of influence parameters being associated with an image of the target region representing a particular anatomical configuration of the target region, obtaining an image of the target region acquired by an imaging unit, the planning unit selecting the set of influence parameters from the stored sets on the basis of a comparison between the acquired image and at least one of the images associated with the sets of influence parameters, and the planning unit adapting the treatment plan on the basis of the selected set of influence parameters.

In a further aspect, the invention suggests a computer program comprising program code means for instructing at least one processor to carry out the method, when the computer program is executed on the processor.

It shall be understood that the system of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
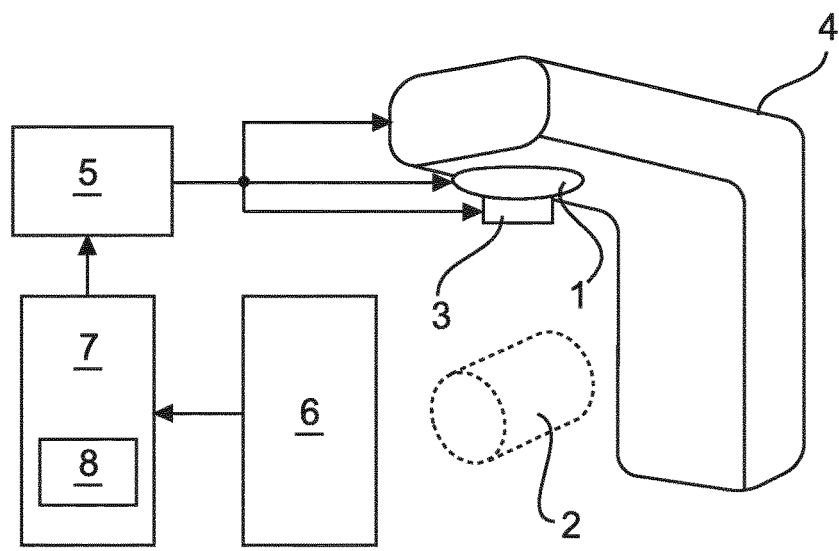
FIG. 1 schematically and exemplarily shows a system for adapting a treatment plan for a radiotherapy treatment, and FIG. 2 schematically and exemplarily shows the k-th view of a radiation treatment and the preceding and subsequent views as well as associations between the views and different dose distributions.

FIG. 1 schematically and exemplarily illustrates an embodiment of a radiation therapy system for delivering radiation treatments to tumors or other diseased target structures within a human or animal patient body.

In the illustrated embodiment, the radiation therapy system comprises a radiation source 1, which can be operated to emit ionizing radiation to be delivered to a region of the patient body including the target structure. In order to deliver the radiation, the patient body is positioned in a treatment zone 2 of the system on a support, which may be configured as a patient table.

The radiation source 1 may include an x-ray tube or a linear particle accelerator for producing one or more ionizing radiation beam(s). The radiation source 1 is controllable in order to vary the intensity and/or energy of the radiation beam. Further, the radiation source 1 may be provided with a collimator 3 for shaping the radiation beam. The collimator 4 may particularly allow varying the radiation intensity across the radiation beam in a defined way. For this purpose, the collimator 3 may be configured as a so-called multi-leaf collimator. The collimator is preferably likewise controllable to change the shape of the radiation beam during the treatment.

Further, the relative position and/or orientation of the radiation source 1 with respect to the body or target structure can be varied in order to change the position at which the radiation beam enters the body surface and/or the angle under which the beam enters the body. For this purpose, the radiation source 1 may be mounted on rotatable gantry 4 so that the radiation source 1 can be rotated around the treatment zone or body within a certain angular range, which may be 360° or less. In addition, the gantry 4 and/or the patient table may be movable back and forth in a direction parallel to the rotation axis of the gantry 4. In addition, it may also be possible to rotate the patient table around an axis perpendicular to the rotation axis of the gantry 3.

For controlling the radiation source 1 and the collimator 3 to set a certain beam configuration and for controlling the gantry 4 and the patient table to adjust the relative position between the target region of the patient body and the radiation source 1, the system include a control unit 5. Preferably, the control unit 5 is implemented in a processor unit including a microprocessor for executing a software program comprising the control routines carried out by the control unit 5.

During the radiation treatment, the relative position and/or orientation between the radiation source 1 and the target region of the patient body are varied, where each relative position and orientation is used for a certain time interval. Herein, a certain angular direction of the radiation beam with respect to the target region, i.e. a certain orientation of a connection line between the radiation source 1 and the target region, is also referred to as a "view". In other words, a view corresponds to a certain relation position of the radiation source 1 and the target region. For each view a certain beam configuration (comprising a certain beam shape and certain beam intensity) is provided such that a sufficient radiation intensity is delivered to the target structure and surrounding tissue is spared as much as possible. Further, the radiation treatment may be performed during a plurality of fractions, where the fractions may be delivered on consecutive days or in another cycle. For each fraction, the views and the irradiation parameters defining their associated beam configurations are specified in the treatment plan, which is provided to the control unit 5 and used by the control unit 5 for controlling the delivery of the radiation treatment.

The treatment plan is generated on the basis of three-dimensional images of the target region in accordance with the anatomical configurations of the target region shown in these images. The images are acquired using a suitable imaging modality, such as, for example, computed tomography (CT) imaging or magnetic resonance (MR) imaging. One image, which is also referred to as reference planning image herein, is captured prior to the radiation treatment. On the basis of this image an initial treatment plan is generated in accordance with the anatomical structure of the target region shown in this image. This initial treatment plan is used for controlling the radiation treatment when the treatment starts. In accordance with the present invention, the treatment plan is updated during the radiation treatment in order to take account of changes of the anatomical structure of the target region due to the changes of the delineation of the target structure and/or motion of the target structure. Such updates may be generated between treatment fractions and/or "online" during a treatment fraction.

The updates of the treatment plan are generated using further three-dimensional images of the target region. For acquiring such images, the system comprises an imaging device 6. The imaging device 6 may be an ultrasound device or an MR device, for example, which allows for (essentially) real-time diagnostics. Likewise, the imaging device 6 may be a CT device or use any other suitable imaging technology. In order to capture images of the target region during the radiation treatment, the imaging device 6 is arranged and configured to acquire images of the target region when the patient body is positioned in the treatment zone 2. The images acquired by the imaging device 6 are provided to a planning unit 7, which is configured to update treatment plans in a way described herein below. The planning unit 7 may also be configured as a processor unit including a microprocessor for executing a software program implementing an algorithm for updating the treatment plans. In this regard, the planning unit 7 may be implemented in the same processing unit as the control unit 5 or in a separate processing unit.

For generating and updating the treatment plan, different procedures may be used. In the following, reference will be made to fluence map optimization (FMO). However, the invention is not limited to this procedure and the person skilled in the art will recognize that the invention can be applied in connection with other procedures in a similar way.

In FMO, the generation of a treatment plan generally involves the determination of a three-dimensional dose distribution d(x) which ensures that the prescribed radiation dose is delivered to the target structure and that surrounding tissue, particularly surrounding OARs, receive the lowest possible radiation dose. The dose distribution d(x) can be computed from an influence matrix M and a fluence vector $\varphi$ as $d(x)=M \cdot \varphi$. Thus, the radiation dose $d_i$ absorbed by a voxel i can be calculated in accordance with $$d_i = \sum_j M_{ij} \cdot \varphi_j \qquad (1)$$

The components $\varphi_j$ of the fluence vector $\varphi$ specify the fluence values of beamlets j, where each beamlet corresponds to a portion of the radiation beam and where the fluence of a beamlet corresponds to its radiation energy integrated over time. Each component $M_{ij}$ of the influence matrix M quantifies the amount of dose absorbed by the voxel i per unit intensity emission from the beamlet j.

For each view, one fluence vector $\varphi_k$ may be determined, and the fluence vectors of all N views may be represented as one vector by stacking the fluence vectors $\varphi_k$. Thus, the overall fluence vector may be given as $\varphi=(\varphi_0, \varphi_1, \ldots, \varphi_{N-1})$. Similarly, the overall influence matrices for all views may be stacked within an overall influence matrix so that the overall influence Matrix M has the form $M=(M^0 \; M^1 \; \ldots \; M^{N-1})$. The influence matrices $M^k$ for the views may be equal to each other. This will particularly be the case, when no changes of the anatomical structure of the target region are taken into consideration in the planning procedure.

The influence matrix M is a function of the anatomical configuration of the target region. In principle, the influence matrix M can be calculated by means of a ray tracing for all beamlets, where the deposited energies are estimated for the voxels included in the ray paths in accordance with their physical properties with respect to the interaction with the radiation. These properties can particularly be quantified using the mass attenuation coefficient. For calculating the influence matrix, any procedure known to a person skilled in the art can be used. For examples, approaches for calculating the influence matrix are described in T. Bortfeld, W. Schlegel, B. Rhein, "Decomposition of pencil beam kernels for fast dose calculations in three-dimensional treatment planning" Med. Phys., 20(2), 311 (1993), and in T. R. McNutt, T. R. Mackie, Paul Reckwerdt, and Bhudatt R. Paliwal, "Modeling Dose Distributions from Portal Dose Images using the Convolution/Superposition Method," Med. Phys. 1996; 23-28, as well as in other works of T. R. Mackie. Further, algorithms for calculating the influence matrix are also implemented in commercially available treatment planning software, such as the software "Pinnacle³" by Philips.

In FMO, the treatment plan is found by determining a fluence vector resulting in an optimal dose distribution, on the basis of a given influence matrix M for the anatomical configuration of the target region. The influence matrix M is separately determined in a preceding step on the basis of a three-dimensional image showing the anatomical configuration of the target region. The views to be used during the radiation treatment may be determined before the treatment plan is generated so that the treatment plan is generated on the basis of specified views.

In order to determine the desired fluence vector, an objective functional $f(d(\varphi))$ may be minimized, which is produced on the basis of the prescribed dose objectives and which may be a weighted sum of individual objective functionals $f_n$ corresponding to the individual dose objectives. For example, these dose objectives may specify a minimum dose $d_{min}$ to be delivered to voxels of the target structure or a maximum dose $d_{max}$ to be delivered to voxels an OAR. Such objectives may be represented by piecewise quadratic cost functional of the form $$f_n \sim \sum_i H(d_{min} - d_i) \cdot (d_{min} - d_i)^2 \text{ or}$$

$$f_n \sim \sum_i H(d_i - d_{max}) \cdot (d_i - d_{max})^2,$$

where the sum is calculated over all voxels i of the volume including the relevant structure and H(x) is the Heaviside function defined as $$H(x) = \begin{cases} 0, & x < 0 \\ 1, & x \geq 0 \end{cases}$$

In addition, prescribed constraints may be taken into account when minimizing the objective functional. Such constraints may provide for a required maximum dose in an OAR and/or a minimum dose in the target structure.

The dose objectives and constraints may be specified by the treatment planner through a graphical user interface. Prior to specifying the dose objective and constraints, the target structure and the relevant OARs may be delineated in a three-dimensional image of the target region in an automatic, semi-automatic or manual delineation procedure. On the basis of the delineations, the treatment planner may then specify the dose objectives and constraints along with the voxels to which they refer (i.e. the voxels of the relevant anatomical structures of the target region).

The objective functional may be minimized automatically using a suitable numerical minimization algorithm, or in a user-guided iterative procedure. In each step of this procedure, a dose distribution minimizing the objective functional is approximated and then reviewed by the treatment planner. In case the treatment planner is not satisfied with the calculated dose distribution, the treatment planner may modify one or more parameters of the calculation (e.g. the planner may modify one or more objectives and/or constraints). Then, a new dose distribution is calculated in the next iteration step, and the process is repeated until the treatment planner accepts the calculated dose distribution.

The calculated optimized dose distribution corresponds to an optimized fluence vector in accordance with equation (1). On the basis of the optimized fluence vector, the planning system determines the machine parameters of the radiation source 1 and the collimator 3 such that the optimized fluence vector is approximately achieved. Such machine parameters include the configuration of the multi-leaf collimator (e.g. the leaf positions) and the beam intensities for each view. In one embodiment of the present invention, a planning system, which may be the planning unit 7 of the radiation therapy system or a separate planning system, generates initial treatment plan using conventional FMO prior to the radiation treatment. The treatment plan is generated using an image of the target region which is referred to as initial planning image herein below. This image may be acquired by means of the imaging device 6 of the radiation therapy system or by means of another imaging device. As explained above, the delineations of the target structure are particularly determined in this image, and the image is used for calculating the influence matrix $M_0$. This influence matrix may be used for all views in the initial planning procedure in one embodiment.

In a further embodiment, changes of the anatomical configuration of the target region may be estimated on the basis of a model for each view, and influence matrices may be generated for the estimated changed anatomical configurations. The initial treatment plan may be generated using these influence matrices for the respective views instead of the influence matrix generated on the basis of the initial planning image.

In order to estimate changes of the anatomical configuration of the target region, changes of the delineation of the target structure may particularly be estimated using a suitable tumor progression model. In principal, any tumor progression model known to the person skilled in the art may be used for this purpose. Examples of tumor progression models are described in S. Nawrocki, B. Zubik-Kowal, "Clinical study and numerical simulation of brain cancer dynamics under radiotherapy", Commun Nonlinear Sci Numer Simulat 22 (2015) 564-573 (doi: 10.1016/j.cnsns.2014.08.001), in G. G. Powathil et al., "Towards Predicting the Response of a Solid Tumour to Chemotherapy and Radiotherapy Treatments: Clinical Insights from a Computational Model", PLoS Comput Biol 9(7): e1003120 (doi: 10.1371/journal.pcbi.1003120), in Y. Liu et al., "Patient Specific Tumor Growth Prediction Using Multimodal Images", Med Image Anal. 2014 April; 18(3): 555-566 (doi: 10.1016/j.media.2014.02.005), and in A. D. Yock et al., "Forecasting longitudinal changes in oropharyngeal tumor morphology throughout the course of head and neck radiation therapy", Medical Physics, 2014 41(8):119-129. Further, a motion path of the target structure may be predicted using a model for the motion of the target structure, if possible, and anatomical configurations may be generated on the basis of the predicted positions of the target structure for each view.

In addition to the generation of the initial treatment plan in accordance with one of the aforementioned embodiments or another technique and preferably also prior to the radiation treatment, the planning system determines possible changed anatomical configurations which the target could have during the radiation treatment. For each possible changed anatomical configuration, the planning system further generates an image and an influence matrix which is associated with the image. Thus, the planning system generates a set of images representing possible anatomical configurations of the target region and associated influence matrices $M_n$. Representations of these images and the associated influence matrices $M_n$ are then stored in a storage 8 of the planning unit 7 of the radiation therapy system. The representations of the images may include the image data in a suitable format or other another representation.

The possible changed anatomical configurations can be generated in any suitable way, and any number of such configurations may be produced. In general, possible changes of the anatomical configurations include changes of the delineations of the target structure and the OARs due to growth and shrinkage thereof and changes of the relative positions of the target structure and the OARs due to displacements and rotations of the target structure and the OARs. All these changes or only a subset thereof may be taken into consideration when producing the possible anatomical configurations. Moreover, the anatomical configurations may be produced only in accordance with geometrical considerations with respect to possible changes. As alternative, more likely changes may be predicted using suitable models as explained above and only such predicted changes may be considered.

Using the selected model, a series of anatomical configurations may be generated which includes estimated delineations for consecutive points in time during the radiation treatment. These points in time may correspond to the scheduled times for the views and/or fractions of the radiation treatment. This also allows to reuse results of the estimation of changes of the anatomical configuration made in order to generate the initial treatment plan, if the initial treatment plan is produced using such estimates.

Further, a motion path of the target structure may be predicted using a model for the motion of the target structure, and anatomical configurations may be generated in which the target structure is positioned at certain positions along the predicted motion path. The positions may be selected such that there is a predefined distances between adjacent positions. For each possible combination of a position and a delineation of the target structure one anatomical configuration may be generated. In the generated anatomical configurations, changes of the positions and/or delineations of OARs in the vicinity of the target structure may also be included.

For some potential target structures, such as the prostate, recent studies suggested that motions of such target structures follow a random walk. In case of such a random motion of the target structure, a regular three-dimensional grid of possible positions may be established in one embodiment. For each position, a series of anatomical configurations may be generated in which the target structure is located at the relevant positions and has several possible delineations. Also in this embodiment, changes of the positions and/or delineations of OARs in the vicinity of the target structure may be included in the generated anatomical configurations.

The images of the target region corresponding to the possible changed anatomical configurations may be generated on the basis of the initial planning image. For each changed anatomical configuration, the planning system may determine a deformation field for transforming the initial planning image into an image showing the anatomical configuration of the target structure. In particular, the deformation field may specify a transformation vector for each voxel that specifies how to transform the voxel to arrive to at the image showing the changed anatomical configuration.

The influence matrices corresponding to the possible changed anatomical configurations may be determined in the same way as the influence matrix corresponding to the original anatomical configuration of the target region as shown in the initial planning image.

Upon having stored the representations of the generated images and the associated influence matrices in the storage 8 of the planning unit 7, the radiation therapy may be started. This is done on the basis of the treatment plan generated on the basis of the initial planning image, which treatment plan is forwarded to the control unit 5 for this purpose. During the radiation treatment the planning unit 7 carries out an update procedure at predefined points in time. In the update procedure, the planning unit 7 checks whether the treatment plan needs to be updated due to changes of the anatomical configuration of the target region and, in case the planning unit 7 determines a need for updating the treatment plan, it generates a revised treatment plan and forwards the revised treatment plan to the control unit 5. The radiation treatment is then continued on the basis of the revised treatment plan until the planning unit 7 updates the treatment plan again at one of the predetermined points in time or until the radiation treatment is finished.

In one embodiment, the planning unit 7 may carry out the update procedure in regular predetermined time intervals. In a further embodiment, an update procedure may be carried out prior to certain portions of the radiation treatment, such as fractions and/or views. In the following, the update procedure will be explained in more detail in connection with an embodiment in which it is carried out for each view of the radiation treatment. In this embodiment, the planning unit 7 effectively determines an optimized treatment plan for each view on the basis of the anatomical configuration of the target region for this view. In this regard, it will be explained herein below how the update procedure is carried out for the k-th view, where k may be any number between 1 and the overall number of views of the radiation treatment.

In order to carry out the update procedure for the k-th view, an image of the target region is acquired by means of the imaging device 6. Preferably, the image is acquired just prior to the k-th view so that the update procedure is carried out on the basis of a current image of the target region showing the actual anatomical configuration of the target region in the k-th view. Further, the planning unit 7 compares the acquired image with the image stored in the storage 8 of the planning unit in order to determine the stored image which has the greatest similarity with the acquired image in accordance with a predefined similarity measure. If the stored images have been generated based on a model for predicting changes of the target structure and/or the OARs, the predicted image for the k-th view may have the greatest similarity with the acquired image. However, due to effects not taken into account by the used model, this does not necessarily have to the case and the planning unit 7 may select another stored image as a result of the comparison with the acquired image.

For comparing the images, any similarity measure known to a person skilled in the art for comparing images can be used. In particular, an image-based, a geometry-based and/or an anatomy-based similarity measure may be used. In one exemplary embodiment, the planning unit 7 may determine one or more parameter(s) of the delineation of the target structure and preferably also of OARs in the acquired image and compares these parameters with the corresponding parameters in the stored images. Examples of such parameters include the maximum diameter of the target structure or OAR, the volume of the target structure or OAR, or the position of the target structure or OAR. In a further exemplary embodiment, landmarks are assigned to the delineation of target structure and preferably also to delineations of structures at risk in the acquired image and in the stored images, and the resulting landmark patterns are compared with each other. For this purpose, a similarity parameter may be calculated for the landmark pattern in each image and this similarity parameter may be compared with the corresponding similarity parameter determined for the estimated delineation of the target structure. For instance, the similarity parameter may be calculated on the basis of a feature vector for each landmark pattern. For each landmark point, the feature vector may comprise the distance between the landmark point and a predefined anchor point. Moreover, the feature vector may include the aforementioned parameters (e.g. the maximum diameter, volume and/or position) of the target structure and/or the relevant OARs. The similarity parameter may then be computed as a function of the components of the feature vector, which may include different weights for the components relating to the target structure and the components relating to different structures at risk.

In order to determine the landmark pattern for the acquired image and the stored images in the aforementioned embodiment, the landmark points may be specified for the initial planning image. For the stored images, the landmark patterns can be determined by transforming the landmark pattern of the initial planning image using the aforementioned deformation fields specifying the transformation between the initial planning image and the stored images. In such a way, the landmark patterns for the stored images may already be determined prior to the radiation treatment and stored along with the images in the storage 8 of the planning unit 7. Further, the planning unit 7 may register the initial planning image including the landmark pattern to the acquired image in order to determine the landmark pattern for the acquired image.

In further embodiments, image-based similarity measures may be used for comparing the images. Such similarity measures may be derived from voxel intensities in the images. In one example, such a similarity measure can be calculated on the basis of the sum of the squared differences (SSD). Here, a difference between the intensity of a voxel in one image and intensity of the corresponding voxel of the other image is calculated for each voxel and the sum of the squared differences is calculated as the similarity measure. Further examples of image-based similarity measures include the normalized cross correlation of the images and the mutual information related to the entropy of the images.

Upon having determined the stored image having the greatest similarity, the planning unit 7 determines an updated treatment plan in accordance with the selected image (in case the selected image differs from image on the basis of which the current treatment plan has been generated). For this purpose, the planning unit 7 determines the influence matrix associated with the selected image, which is referred to as $M_{n(k)}$ herein below. Moreover, the planning unit 7 generates the updated treatment plan on the basis of the previously used treatment plan, particularly for controlling the treatment in the (k−1)-th view. In addition, the planning unit 7 may optionally calculate the new treatment plan on the basis of the original treatment plan generated on the basis of the initial planning image. The updated treatment plan is generated for controlling the radiation treatment in the k-th view and does preferably also specify the irradiation parameters for subsequent view of the radiation treatment. The latter is preferred, because the planning procedure does generally have to take into consideration the complete radiation treatment in order to calculate the proper dose distribution for any view.

More specifically, the planning unit 7 may in principal determine the updated treatment plan by minimizing the dose objective functional $$f(\varphi_k) = f(d^p(k) + d^k + d^f(k)), \quad (2)$$

in order to determine a fluence vector $\varphi_k$ on the basis of which the new treatment plan is calculated, where $d^k$ denotes the dose distribution for the k-th view and $d^p(k)$ and $d^f(k)$ denote the cumulated dose distributions for the previous views and the future views, i.e.:

$$d^p(k) = \sum_{i=0}^{k-1} d^i \text{ and } d^f(k) = \sum_{i=k+1}^{N-1} d^i$$

Figure 2:
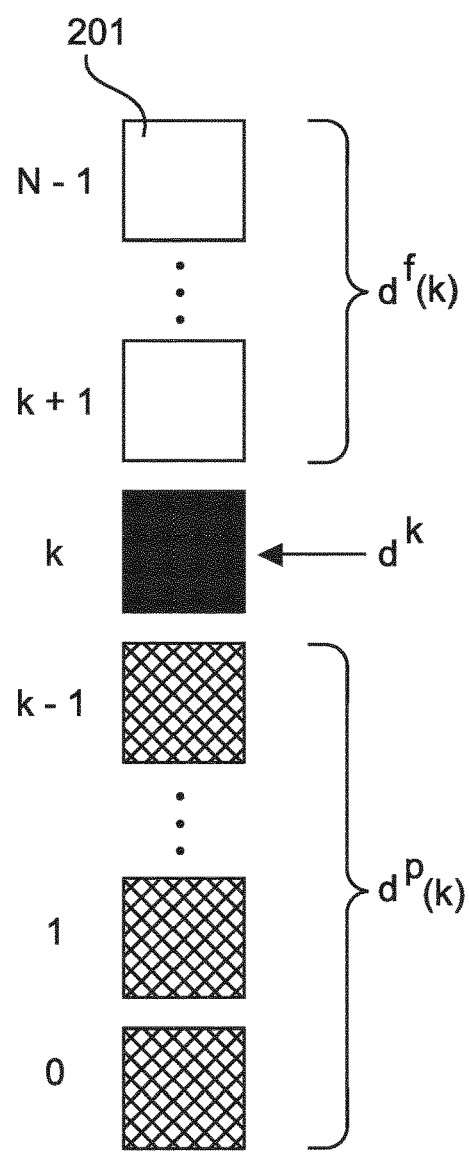

This is also illustrated in FIG. 2 schematically showing the views 21 of a radiation treatment and the associated dose distribution.

The dose objective functional f may correspond to the dose objective function used for determining the initial treatment plan. Since a dose distribution minimizing this functional has already been determined when the initial treatment was generated, the planning unit 7 may also determine the updated treatment plan by minimizing a difference between the previously generated dose distribution and the updated dose distribution $d^p(k) + d^k + d^f(k)$ in accordance with a suitable difference measure. In particular, a least-square difference measure may be used. Thus, the fluence vector $\varphi_k$ for determining the updated treatment plan may be calculated as $$\varphi_k = \underset{\varphi_k}{\operatorname{argmin}} \| d^p(k) + d^k + d^f(k) - d^{plan} \|^2, \quad (3)$$

where $d^{plan}$ is the dose distribution minimizing the objective functional used for generating the initial treatment plan. When the fluence vector $\varphi_k$ is determined in such a way, the computational complexity can be reduced compared with the calculation on the basis of equation (2). Moreover, it is possible to determine a new dose distribution which is similar to the dose distribution generated in the initial treatment planning, which may have been reviewed and approved by a treatment planner.

In order to determine the dose distribution $d^p(k)$ in equations (2) and (3), the planning unit 7 may store the dose distributions $d^i$ determined for the previous views, or the planning unit 7 may calculate the dose distribution $d^p(k)$ from the fluence vectors $\varphi_i$ of the previous views and the influence matrices $M^i$ used for calculating these fluence vectors:

$$d^p(k) = \sum_{i=0}^{k-1} M_{n(i)} \cdot \varphi_i. \quad (4)$$

When calculating $d^p(k)$ from the distributions in accordance with equation (3), the dose distributions may be transformed using a transformation reflecting the changes of the anatomical structure of the target region compared with the anatomical structure shown in the initial planning image (underlying $d^{plan}$). This transformation may be made on the inverses of the deformation fields for transforming the initial planning image into the images selected for the treatment plan update for the previous views. These inverse deformation fields may be calculated prior to the radiation treatment and may be stored in the storage 8 of the planning unit in association with the images.

The dose distribution $d^k$ in equations (2) and (3) is given by the product of the fluence vector $\varphi_k$ to be determined and the influence matrix $M_n$ associated with the selected stored image: $d^k = M_n \cdot \varphi_k$. This influence matrix $M_n$ is read from the storage 8 by the planning unit 8 and used for determining the updated treatment plan upon having selected a stored image.

The future dose distribution $d^f(k)$ may be calculated on the basis of the fluence vectors $\varphi_i^0$ for the future views, which have been determined in the initial treatment planning procedure. This does particularly allow for pre-computing the future dose distribution $d^f(k)$ as will be explained in more detail herein below and, thus, significantly reduces the computational complexity for updating the treatment plan. Moreover, several anatomical configurations of the target region may be used as a basis for determining the future dose distribution $d^f(k)$. In the following three possible approaches will be explained, which are referred to as static approach, quasi-static approach and dynamic approach hereinafter.

In accordance with the static approach, the dose distribution $d^f(k)$ is calculated under the assumption that the anatomical structure of the target region in the future views corresponds to the anatomical structure as shown in the initial planning image. Thus, the dose distribution $d^f(k)$ is calculated as $$d^f(k) = \sum_{i=k+1}^{N-1} M_0 \cdot \varphi_i^0 \quad (5)$$

Thus, there is one future dose distribution $d^f(k)$ for each view, independent of the selected stored image. For each view, this dose distribution may be computed prior to the radiation treatment and stored in the storage 8 of the planning unit 7.

While it particularly reduces computational complexity, the static approach does only provide inaccurate estimates of the dose distribution $d^f(k)$. However, it is to be noted that these estimates will be corrected by the planning unit 7 in each view. Therefore, also the static approach can lead to satisfactory results for the treatment plan.

In accordance with the quasi-static approach, the dose distribution $d^f(k)$ is calculated under the assumption that the anatomical structure of the target region in the future views corresponds to the anatomical structure as shown in the selected image. Consequently, the dose distribution $d^f(k)$ is calculated using the influence matrix $M_{n(k)}$ associated with the selected image:

$$d^f(k) = \sum_{i=k+1}^{N-1} M_{n(k)} \cdot \varphi_i^0 \quad (6)$$

The quasi-static approach provides a more accurate estimate of the future dose distribution compared with the static approach. In this approach, there is one future dose distribution $d^f(k)$ for each view and for each selected image. As in the static approach, these dose distributions may be pre-computed prior to the radiation treatment and for each image the dose distributions for the different views may be stored in the storage 8 of the planning unit 7 in association with the image.

In accordance with the dynamic approach, the dose distribution $d^f(k)$ is estimated on the basis of predications of the anatomical structure of the target region for each future view. These predications may be determined on the basis of a suitable model as already explained above. In this approach, a specific influence matrix is used for each future view. When the influence matrices for these views are denoted as $M_{n(i)}$, i=k+1, ..., N−1, the dose distribution $d^f(k)$ is calculated according to $$d^f(k) = \sum_{i=k+1}^{N-1} M_{n(i)} \cdot \varphi_i^0 \tag{7}$$

This approach may particularly be used in case the stored images are generated on the basis of a predictive model as explained above. Further, this approach allows for an even more accurate estimate of the future dose distribution. However, it also involves a higher computational complexity for determining the influence matrices $M_{n(i)}$ and the future dose distributions. As in the quasi-static approach, there one future dose distribution $d^f(k)$ for each view and for each selected image in the dynamic approach, and the possible future dose distributions may be pre-computed prior to the radiation treatment and for each image the dose distributions for the different views may be stored in the storage 8 of the planning unit 7 in association with the image.

The future dose distribution calculated in accordance with one of the aforementioned procedures may be inaccurate to a smaller or larger amount depending on the selected procedure. However, possible inaccuracies of the future dose distribution are corrected in subsequent updating steps for the treatment plan. Moreover, the influence of an inaccurately calculated future dose distribution on the treatment plan diminishes in each updating step since future dose is reduced in each step. Thus, any inaccuracies of the calculation of future dose distribution does not deteriorate the quality of the radiation treatment. In accordance with the embodiments explained above, the planning unit can determine a fluence vector $\varphi_k$ for the k-th view of the radiation treatment e.g. by minimizing the functional provided in equation (2) or (3). On the basis of the fluence vector, the planning unit 7 may then determine corresponding machine or irradiation parameters for the k-th view which may be included into the updated treatment plan. For the subsequent views, the irradiation parameters from the initial treatment plan may be maintained. In the described embodiments, the fluence vector $\varphi_k$ for the k-th view is the only variable, when minimizing the relevant functional in the planning unit 7. Thus, the update of the treatment plan for the k-th view involves a relatively low computational complexity.

In accordance with the described embodiments, the planning unit 7 may update the treatment plan for the views of the radiation treatment to account for changes of the anatomical configuration of the target region. Thus, a "single view optimization" of the treatment is effectively provided, which provides optimized irradiation parameters for the views substantially in real time on the basis of acquired images of the target region.

Generally, the planning unit 7 may perform the update procedure explained above prior to each view so that the irradiation parameters can be optimized for each view.

However, due to the inherent latency of the imaging device 6, a current image of the target region may not be available prior to each view. In case no image is available, the planning unit 7 may perform the update procedure on the basis of the last acquired image of the target region. Moreover, in order to minimize degradation of the optimization for future views, the planning unit may perform an additional determination of the fluence vector for the relevant in accordance with the above update procedure, when a more recent image of the target region becomes available. This fluence vector is then used for determining the past dose distribution $d^p$ when optimizing the irradiation parameters for subsequent views.

Further, while the embodiments described above relate to FMO, similar procedures for updating the treatment plan can be used in connection with other optimization techniques.

One such technique is direct machine parameter optimization (DMPO). In DPMO, the machine parameters of the radiation source 1 and the collimator 3 are directly optimized instead of optimizing the fluence vectors. Hereby, possible degradations due to the conversion of the fluence vectors into machine parameters can be avoided. In order to determine the machine parameters, an objective functional of the machine parameters is minimized, which is determined in a similar way as the above described function of the fluence vector. As the person skilled in the art will appreciate, the above-described update procedure can thus be carried out in a similar way in connection with DPMO.

Further, the update procedure can similarly applied to volumetric modulated arc therapy (VMAT), where the radiation source 1 rotates around the target regions and the beam configuration is continuously varied during the rotation. When applying the procedure to VMAT, updates of the treatment plan may be made at a certain number of angular positions of the radiation source, which correspond to the views explained before. The distance between these positions may be selected such that there is enough time for performing the required calculations in each step.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for adapting a radiotherapy treatment plan for treating a target structure within a target region of a patient body, the radiotherapy treatment plan comprising irradiation parameters for controlling a delivery of radiation to the target region, the system comprising:
   a planning unit configured to adapt the radiotherapy treatment plan on a basis of a set of influence parameters quantifying an influence of the radiation on the target region per unit intensity emission in accordance with an anatomical configuration of the target region, a storage for storing a plurality of sets of influence parameters, each set being associated with an image of the region of the patient body representing a particular anatomical configuration of the target region, and an imaging unit configured to acquire an image of the region of the patient body, wherein the planning unit is configured to select the set of influence parameters from the stored sets on the basis of a comparison between the captured image and at least one of the images associated with the sets of influence parameters.

2. The system as defined in claim 1, wherein the radiotherapy treatment plan is delivered in a plurality of time intervals and wherein the planning unit is configured to determine updated irradiation parameters for controlling the delivery of the radiation to the target structure in a k-th time interval.

3. The system as define in claim 2, wherein the planning unit is configured to determine only the irradiation parameters for the k-th time interval on the basis of the selected set of influence parameters.

4. The system as defined in claim 2, wherein a relative orientation between a radiation beam and the target structure changes during the radiotherapy treatment, and wherein each time interval corresponds to a period with a constant relative orientation between the radiation beam and the target structure.

5. The system as defined in claim 2, wherein the planning unit is configured to determine the irradiation parameters on the basis of a radiation dose distribution delivered to the target region prior to the k-th time interval.

6. The system as defined in claim 2, further being configured to provide an estimate of a radiation dose distribution delivered to the target region in subsequent time intervals following the k-th time interval, wherein the planning unit is configured to determine the irradiation parameters for the k-th time interval on the basis of said estimate.

7. The system as defined in claim 6, wherein the estimate is derived from an initial treatment plan determined prior to the radiotherapy treatment.

8. The system as defined in claim 6, wherein the estimate of the radiation dose distribution is based on one predetermined anatomical configuration of the target region.

9. The system as defined in claim 6, further being configured to provide plural estimates of the radiation dose distribution delivered to the target region in subsequent time intervals, each estimate being associated with the k-th time interval and one set of influence parameters, wherein the planning unit is configured to determine the radiotherapy treatment plan on the basis of the estimate associated with the selected set of influence parameters.

10. The system as define in claim 9, wherein the estimates are based on predictions of the anatomical configuration of the target region in the subsequent time intervals, the predication being made using a model quantifying changes of the anatomical configuration of the body as a function of time.

11. The system as defined in claim 6 wherein the estimate or plural estimates are pre-stored in the storage.

12. The system of claim 6, wherein the estimate is derived from an emitted fluence specified in an initial treatment plan for the subsequent time intervals.

13. The system as defined in claim 1, wherein the planning unit is configured to select the set of influence parameters associated with an image that has the largest similarity with the captured image in accordance with a predefined similarity measure.

14. The system as defined in claim 1, wherein each set of influence parameters comprises components of an influence matrix.

15. A method for adapting a radiotherapy treatment plan for treating a target structure within a target region of a patient body, the radiotherapy treatment plan comprising irradiation parameters for controlling a delivery of radiation to the target region, the method comprising:

storing a plurality of sets of influence parameters in a planning unit, the influence parameters quantifying an influence of the radiation on the target region per unit intensity emission in accordance with an anatomical configuration of the target region and each set of influence parameters being associated with an image of the target region representing a particular anatomical configuration of the target region, obtaining an image of the target region acquired by an imaging unit, the planning unit selecting the set of influence parameters from the stored sets on a basis of a comparison between the acquired image and at least one of the images associated with the sets of influence parameters, and the planning unit adapting the radiotherapy treatment plan on the basis of the selected set of influence parameters.

16. A tangible, non-transitory computer readable medium having stored thereon software instructions that, when executed by a processor, cause the processor to perform a method for adapting a radiotherapy treatment plan for treating a target structure within a target region of a patient body, the radiotherapy treatment plan comprising irradiation parameters for controlling a delivery of radiation to the target region, the method comprising:

storing a plurality of sets of influence parameters in a planning unit, the influence parameters quantifying an influence of the radiation on the target region per unit intensity emission in accordance with an anatomical configuration of the target region and each set of influence parameters being associated with an image of the target region representing a particular anatomical configuration of the target region;

obtaining an image of the target region acquired by an imaging unit; and selecting, by the planning unit, the set of influence parameters from the stored sets on a basis of a comparison between the acquired image and at least one of the images associated with the sets of influence parameters, the planning unit adapting the radiotherapy treatment plan on the basis of the selected set of influence parameters.

17. An apparatus for adapting a radiotherapy treatment plan for treating a target structure within a target region, the treatment plan comprising irradiation parameters for controlling a delivery of radiation to the target region, the apparatus comprising:

a controller comprising a processor; and a memory that stores instructions, which, when executed by the processor, cause the controller to:

store a plurality of sets of influence parameters in a planning unit, the influence parameters quantifying an influence of the radiation on the target region per unit intensity emission in accordance with an anatomical configuration of the target region, wherein each set of influence parameters are associated with an image of the target region representing a particular anatomical configuration of the target region;

obtain an image of the target region acquired by an imaging unit; and select, by the planning unit, the set of influence parameters from the stored sets on a basis of a comparison between the acquired image and at least one of the images associated with the sets of influence parameters, the planning unit being adapted the treatment plan on the basis of the selected set of influence parameters.

18. The apparatus as defined in claim 17, wherein the radiotherapy treatment plan is delivered in a plurality of time intervals, and the planning unit is configured to determine updated irradiation parameters for controlling the delivery of the radiation to the target structure in a k-th time interval.

19. The system as define in claim 18, wherein the planning unit is configured to determine only the irradiation parameters for the k-th time interval on the basis of the selected set of influence parameters.

20. The system as defined in claim 18, wherein a relative orientation between a radiation beam and the target structure changes during the radiotherapy treatment, and each time interval corresponds to a period with a constant relative orientation between the radiation beam and the target structure.

\* \* \* \* \*